US006351987B1

(12) United States Patent
Winston et al.

(10) Patent No.: US 6,351,987 B1
(45) Date of Patent: Mar. 5, 2002

(54) FIBER OPTIC PRESSURE SENSOR FOR DC PRESSURE AND TEMPERATURE

(75) Inventors: Charles R. Winston; Daniel L. Gysling, both of Glastonbury; Mark R. Myers, Storrs; Alan D. Kersey, S. Glastonbury; Rebecca S. McGuinn, Middletown, all of CT (US)

(73) Assignee: CiDRA Corporation, Wallingford, CT (US)

( * ) Notice: Subject to any disclaimer, the term of this patent is extended or adjusted under 35 U.S.C. 154(b) by 0 days.

(21) Appl. No.: 09/548,792

(22) Filed: Apr. 13, 2000

(51) Int. Cl.[7] ............................ G01N 11/00; E21B 47/12
(52) U.S. Cl. .................................. 73/53.01; 73/152.02
(58) Field of Search ................ 73/53.01, 38, 152.02, 73/152.18, 152.22, 152.27; 250/227.14, 40.5 A, 227.17; 385/12, 13

(56) References Cited

U.S. PATENT DOCUMENTS

| 4,080,837 A | 3/1978 | Alexander et al. |
| 4,114,439 A | 9/1978 | Fick |
| 4,308,746 A | 1/1982 | Covington ............... 73/40.5 R |
| 4,950,883 A | 8/1990 | Glenn |
| 4,996,419 A | 2/1991 | Morey |
| 5,115,670 A | 5/1992 | Shen |
| 5,218,197 A | 6/1993 | Carroll |
| 5,317,576 A | 5/1994 | Ball et al. |
| 5,363,342 A | 11/1994 | Layton et al. ............... 367/149 |

(List continued on next page.)

OTHER PUBLICATIONS

Giallorenzi et al, Optical Fiber Sensor Technology, 4/82, IEEE J. Quant. Elect. vol QE–18, No. 4, pp 626–665.
McDearmon, Theoretical Analy. Push–Pull Fiber–Optic Hydrophone, IEEE J Lightwave Tech.,4/87, vol. LT–5, No. 5, pp647–652.

Dandridge et al, "Fiber Optic Sensors for Navy Application," IEEE, Feb. 1991.

Dandrige, et al, "Multiplexed Intereferometric Fiber Sensor Arrays," SPIE, vol. 1586, 1991, pp 176–183.

A.Kersey et al, "Multiplexed Fiber Bragg Grating Strain –Sensor System with a Fabry–Perot Wavelength Filter," Opt Letters, vol. 18, No. 16, Aug. 1993.

*Primary Examiner*—Hezron Williams
*Assistant Examiner*—Jay L. Politzer
(74) *Attorney, Agent, or Firm*—Ware, Fressola, Van Der Sluys & Adolphson LLP

(57) ABSTRACT

A DC pressure and temperature sensor system for sensing and measuring the DC pressure and temperature of a production fluid (such as oil, gas and water mixtures) in tubing, such as tubing used to extract production fluid from a drilled site. The sensor system includes at least one fluid sensor, but sometimes two. Only one is needed if either the DC pressure or temperature of the production fluid (but not both) is provided by an independent measurement. In general, though, the sensor system includes: a first and second fluid sensor, the first using a first sensing material, and the second using a second sensing material in which sound travels at a rate that depends on the DC pressure and temperature of the second sensing material in a measurably different way than for the first sensing material. Each sensing material is coupled to the production fluid, preferably via a thin-walled membrane, so as to be at a DC pressure and temperature that is, preferably, the same as for the production fluid. Each fluid sensor is used to provide information about the speed of sound in its sensing material, and since the speed of sound depends on the DC pressure and temperature of the sensing material, in providing information about the speed of sound, each fluid sensor also provides information about the DC pressure and temperature of the sensing material, which is either the same as that of the production fluid or can be correlated to that of the production fluid.

9 Claims, 2 Drawing Sheets

U.S. PATENT DOCUMENTS

| | | | |
|---|---|---|---|
| 5,399,854 A | 3/1995 | Dunphy et al. | 250/227.17 |
| 5,401,956 A | 3/1995 | Dunphy et al. | |
| 5,426,297 A | 6/1995 | Dunphy et al. | |
| 5,493,390 A | 2/1996 | Verasi et al. | |
| 5,513,913 A | 5/1996 | Ball et al. | |
| 5,564,832 A | 10/1996 | Ball et al. | |
| 5,625,724 A | 4/1997 | Frederick et al. | 385/12 |
| 5,925,879 A | 7/1999 | Hay | 250/40.5 A |
| 6,191,414 B1 | 2/2001 | Ogle et al. | 250/227.14 |
| 6,233,374 B1 | 5/2001 | Ogle et al. | 385/13 |

FIBER OPTIC PRESSURE SENSOR FOR DC PRESSURE AND TEMPERATURE

CROSS REFERENCE TO RELATED APPLICATIONS

The present invention is related to the following U.S. application:

U.S. application, Ser. No. 09/344,094 filed Jun. 25, 1999, and entitled, "FLUID PARAMETER MEASUREMENT IN PIPES USING ACOUSTIC PRESSURES."

The related application is assigned to the present assignee. The subject matter of the related application is hereby incorporated by reference.

FIELD OF THE INVENTION

The present invention pertains to the field of steady state (DC) pressure and temperature measurement. More particularly, the present invention pertains to the field of sensors for measuring steady state pressure and temperature of a moving fluid, such as is used in drilling for oil and natural gas, and especially to sensors using optical fibers and having a Bragg grating.

BACKGROUND OF THE INVENTION

Because of various advantages including for example immunity to electromagnetic interference and especially reliability in a high temperature environment, it is desirable to measure the static or so-called DC pressure and temperature of a moving fluid using sensors based on optical methods. In addition, though, such a sensor should be robust. In case of measuring the pressure and temperature of a moving fluid in a harsh environment, it is advantageous to provide a sensor that will yield precise and accurate measurements over a long period of time, i.e. to provide a sensor whose operating characteristics will not significantly change over a useful lifetime of the sensor even in the harsh environment. One application where a robust DC pressure and temperature sensor is needed is downhole in extracting oil and gas from a drilled site. There it is the DC pressure and temperature of the production fluid (mixtures of oil, gas and water) that is sought to be measured.

In some applications of sensing parameters of a process, optical fibers are wrapped around a mandrel that deforms in response to changes in the process parameter being sensed and measured. To make a robust sensor using optical fibers wrapped around a mandrel that deforms in response to changes in DC pressure or temperature, it is important to keep the optical fibers from being under too high a constant tension, which would cause the optical fibers to undergo creep (involving a failure of the bonding agent adhering the optical fibers to the mandrel) and would also shorten the life of the optical fibers. The prior art does not teach how to keep tension low in optical fibers being used in a mandrel-based DC pressure and temperature sensor, and thus to make a robust mandrel-based sensor.

Thus, what is needed is a robust, optical-fiber-wound, mandrel-based sensor for sensing information about DC pressure and temperature of a moving (flowing) fluid, and in particular for sensing information about DC pressure and temperature of a production fluid in oil and gas extraction from a drilled site.

SUMMARY OF THE INVENTION

Accordingly, the present invention provides a DC pressure and temperature sensor system, for sensing and measuring the DC pressure and temperature of a production fluid in tubing. It includes at least one fluid sensor, but sometimes two. Only one is needed if either the DC pressure or temperature of the production fluid (but not both) is provided by an independent measurement. In case that no such independent information is available, the DC pressure and temperature system includes: a first fluid sensor and a second fluid sensor, the first fluid sensor using a first sensing material (preferably one or another type of oil) and the second fluid sensor using a second sensing material in which sound travels at a rate that depends on the DC pressure and temperature of the second sensing material in a measurably different way than for the first sensing material. Each sensing material is coupled to the production fluid, preferably via a thin-walled membrane, so as to be at a DC pressure and temperature that can at least be correlated to the DC pressure and temperature of the production fluid and is preferably the same as the DC pressure and temperature of the production fluid. Each fluid sensor is responsive to the DC pressure and temperature of the production fluid via the coupling of the production fluid to the sensing materials, and via monitoring the speed of sound in the sensing materials. Each fluid sensor provides sensing signals containing information about the DC pressure and temperature of the production fluid. The information relates directly to the speed of sound in the sensing material of each fluid sensor, and the information from each fluid sensor (two pieces of information) is used to determine the two quantities to be measured: the DC pressure and temperature of the production fluid.

In a further aspect of the invention, at least one of the fluid sensors includes: a mandrel, enclosing the respective sensing material, responsive to changes in DC and acoustical pressure and temperature of the corresponding sensing material, for providing a change in diameter corresponding to changes in DC and acoustical pressure and temperature of the corresponding sensing material; and an array of sensing means affixed to the mandrel, responsive to changes in the diameter of the mandrel, for providing the signals containing information about the DC pressure and temperature of the production fluid.

Essentially, each sensing means in the array of sensing means of a fluid sensor is used to detect the propagation of acoustic waves. Since an array of such sensing means is used, the speed of the acoustic wave (i.e. the speed of sound) in the sensing material can be determined. The speed of sound in a material depends only on the DC pressure and temperature of the material, and so each fluid sensor, by providing a measure of the speed of sound in the sensing material used by the fluid sensor, provides one of two pieces of information needed to determine the two quantities, DC pressure and temperature of the sensing material, the two quantities being the same or correlated (because of coupling through the membrane) as for the production fluid.

In a still further aspect of the invention, at least one sensing means is a winding of an optical fiber about the mandrel, the winding having an associated Bragg grating, and the winding is responsive to a narrowband light signal.

BRIEF DESCRIPTION OF THE DRAWINGS

The above and other objects, features and advantages of the invention will become apparent from a consideration of the subsequent detailed description presented in connection with accompanying drawings, in which.

BEST MODE FOR CARRYING OUT THE INVENTION

Figure 1:
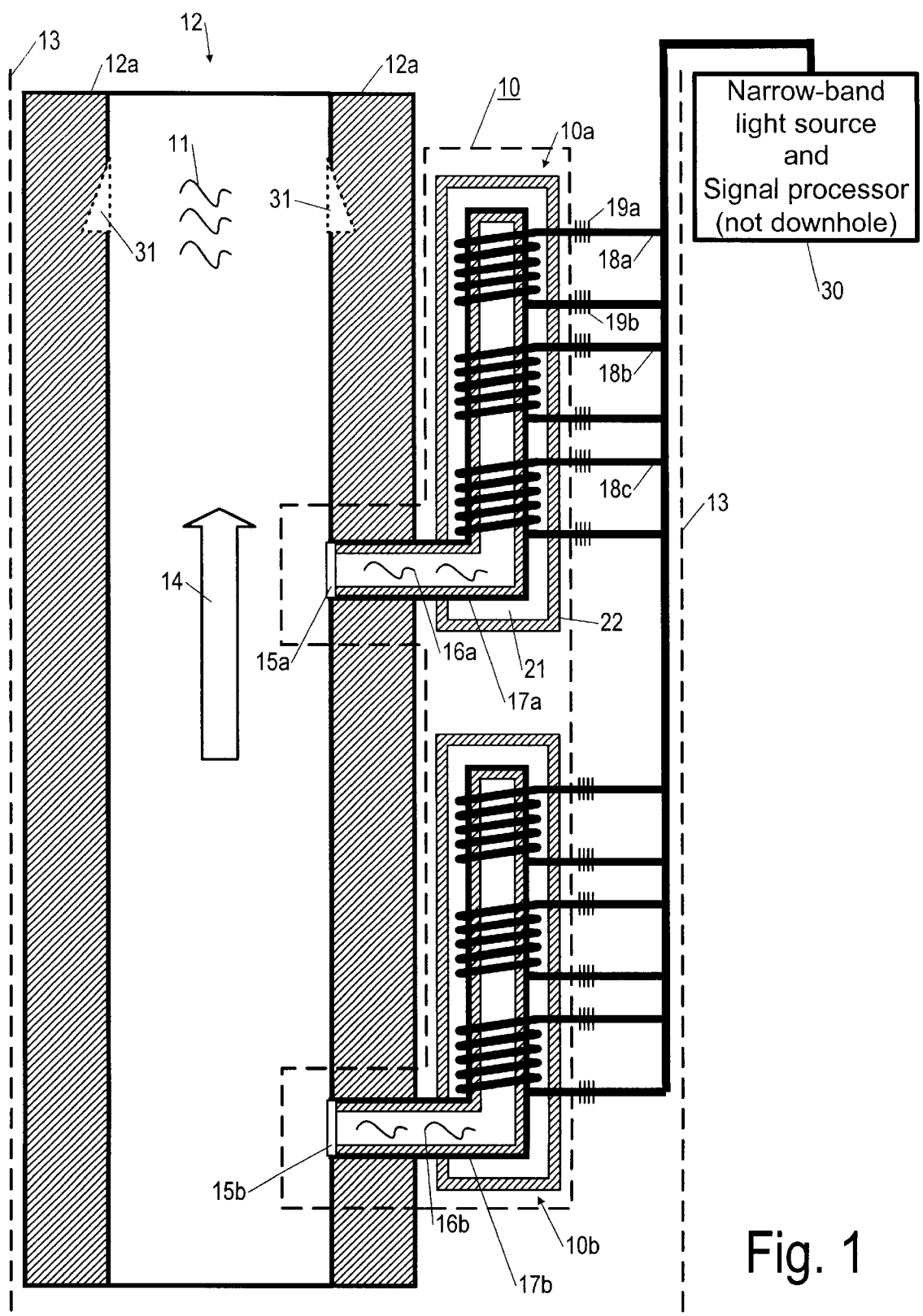
FIG. 1 is schematic diagram of a DC pressure and temperature sensor according to the present invention.

Referring now to FIG. 1, a DC pressure and temperature sensor system 10 is shown being used to measure the DC pressure and temperature of a production fluid 11 (oil, gas and water mixtures) moving through production tubing 12, having production tubing walls 12a, the production tubing in turn enclosed in a casing 13. (The casing, which has substantial walls, is indicated merely by a dashed line.) The production fluid 11 has a direction of flow indicated by an arrow 14.

According to the present invention, a DC pressure and temperature sensor system 10 is affixed to the production tubing walls 12a, inside the casing 13, and includes a first fluid it sensor 10a and a second fluid sensor 10b. The two fluid sensors 10a 10b each include a sensing material 16a 16b within a mandrel 17a 17b. The sensing materials 16a 16b are different, especially in how the velocity of sound in each fluid depends on the temperature and pressure of the production fluid. With the exception that the two sensing materials 16a 16b are different, usually both a kind of oil, the first and second fluid sensors 10a 10b are usually identical. It is important to understand that the sensing material can be a substance different than oil, and can even be a gas. It is only necessary that sound travel at a rate that depends on the DC pressure and temperature of the second sensing material in a measurably different way it depends on the DC pressure and temperature of the first sensing material, as will be explained in more detail below.

The production fluid 11 is in intimate contact with a thin diaphragm or bellows 15a 15b of both the first fluid sensor 10a and the second fluid sensor lob of the DC pressure and temperature sensor system 10. The DC pressure and also the temperature of the production fluid 11 are communicated through each thin diaphragm or bellows 15a 15b to the sensing material 16a 16b within the corresponding fluid sensor 10a 10b. In the preferred embodiment, the sensing materials 16a 16b within each fluid sensor 10a 10b are at the same DC pressure and temperature as the production fluid, but it is only necessary that there be some known correlation between the DC pressure and temperature of the production fluid and that of each of the sensing materials.

The DC pressure and temperature sensor system 10 will now be described specifically with respect to the first fluid sensor 10a, with the understanding that a similar description is appropriate to the second fluid sensor 10b. The first fluid sensor 10a includes a mandrel 17a. The mandrel 17a is wound with optical fibers in at least two different locations, preferably three locations but sometimes more than three locations. The resulting optical fiber windings 18a 18b 18c are used to convert the change in diameter of the mandrel 17a into an optical signal. The mandrel 17a is enclosed in a mandrel housing 22 that protects the mandrel and its array of optical fiber windings from any backpressure that might be exerted by any material in the region 21 outside of the mandrel 17a, between the production tubing walls 12a and the casing 13 for the production tubing 12. Region 21 is a low impedance fluid that acoustically isolates the sensing tube from the surroundings and provides a benign environment for the fibers. Preferably, it is an inert gas at low pressures.

In the preferred embodiment, each optical fiber winding 18a 18b includes a fiber Bragg grating 19a (FBG) at one end of the optical fiber winding 18a and another FBG 19b at the other end of the optical fiber winding 18a. Each FBG is designed to reflect light at or near a particular wavelength. When light from a narrowband light source, part of the narrowband light source and signal processor 30, is introduced into one end of the optical fiber winding 18a, some of the light is reflected by each FBG 19a 19b, and the distance between the two fiber Bragg gratings can be determined interferometrically. The distance between two FBGs 19a 19b in a single winding 18a varies according to the acoustic pressure variations in the sensing material 16. Because of this sensitivity to the acoustic pressure variations in the sensing material, an array of windings 18a 18b 18c can be used to determine the speed of sound in the sensing material 16, as disclosed e.g. in the above-mentioned U.S. Patent application, Ser. No. 09/344,094. The speed of sound in the sensing material 16a is one piece of information needed to determine the DC pressure and temperature of the sensing material, and so also that of the production fluid, since as explained above the sensor system 10 is designed so that the sensing material 16a is at substantially the same DC pressure and temperature as the production fluid 11, or is at a DC pressure and temperature that can be correlated with the DC pressure and temperature of the production fluid.

It is important to understand that unless some independent source of information on either the production fluid temperature or the production fluid DC pressure is available, the DC pressure and temperature sensor system 10 includes both a first fluid sensor 10a and a second fluid sensor 10b. Having a first fluid sensor 10a and a second fluid sensor 10b in combination providing a DC pressure and temperature sensor system 10 is necessary because neither of the individual fluid sensors 10a 10b provide information that in any way distinguishes whether the speed of sound in the sensing materials 16a 16b changes because of a change in DC pressure of the sensing materials or because of change in temperature of the sensing materials or both. If it were possible to distinguish between a change in the speed of sound in the sensing materials 16a 16b on account of a change in DC pressure compared to temperature, then only a single fluid sensor 10a 10b would be needed, because then an equation of state could relate the pressure to the temperature.

As it is, two fluid sensors 10a 10b are used in the following way. In both the first fluid sensor 10a and in the second fluid sensor 10b, the speed of sound is measured. In the preferred embodiment, this is done using information conveyed by optical signals from optical fiber windings 18a 18b 18c as described in the co-pending, related application entitled, "Fluid Parameter Measurement in Pipes using Acoustic Pressures," CiDRA Docket No. CC-0066A. Essentially, the array of optical fiber windings 18a 18b 18c detects a pressure wave associated with the propagation of sound within the first fluid sensor 10a, and the narrowband light source and signal processing module 30 determines the speed of sound in the sensing material 16a, on the basis of when each optical fiber detected the pressure wave. The narrowband light source and signal processing module 30 uses acoustic spatial array signal processing techniques. The sound itself is, in the preferred embodiment, provided usually as a natural by-product of the flow of the production fluid 11 through the production piping 12, coupled into the DC pressure and measurement sensor system 10 through the thin diaphragms or bellows 15a 15b, but can also be forced and tailored by providing vortex shedding sites 31 in the production tubing 12 or other means of acoustic excitation (such as an external noise source, a speaker, or a shaker). It is also possible to customize the acoustic resonant characteristics of the production tubing 12 or the mandrels 17a 17b, or by other means not necessarily requiring an active sound source.

Figure 2:
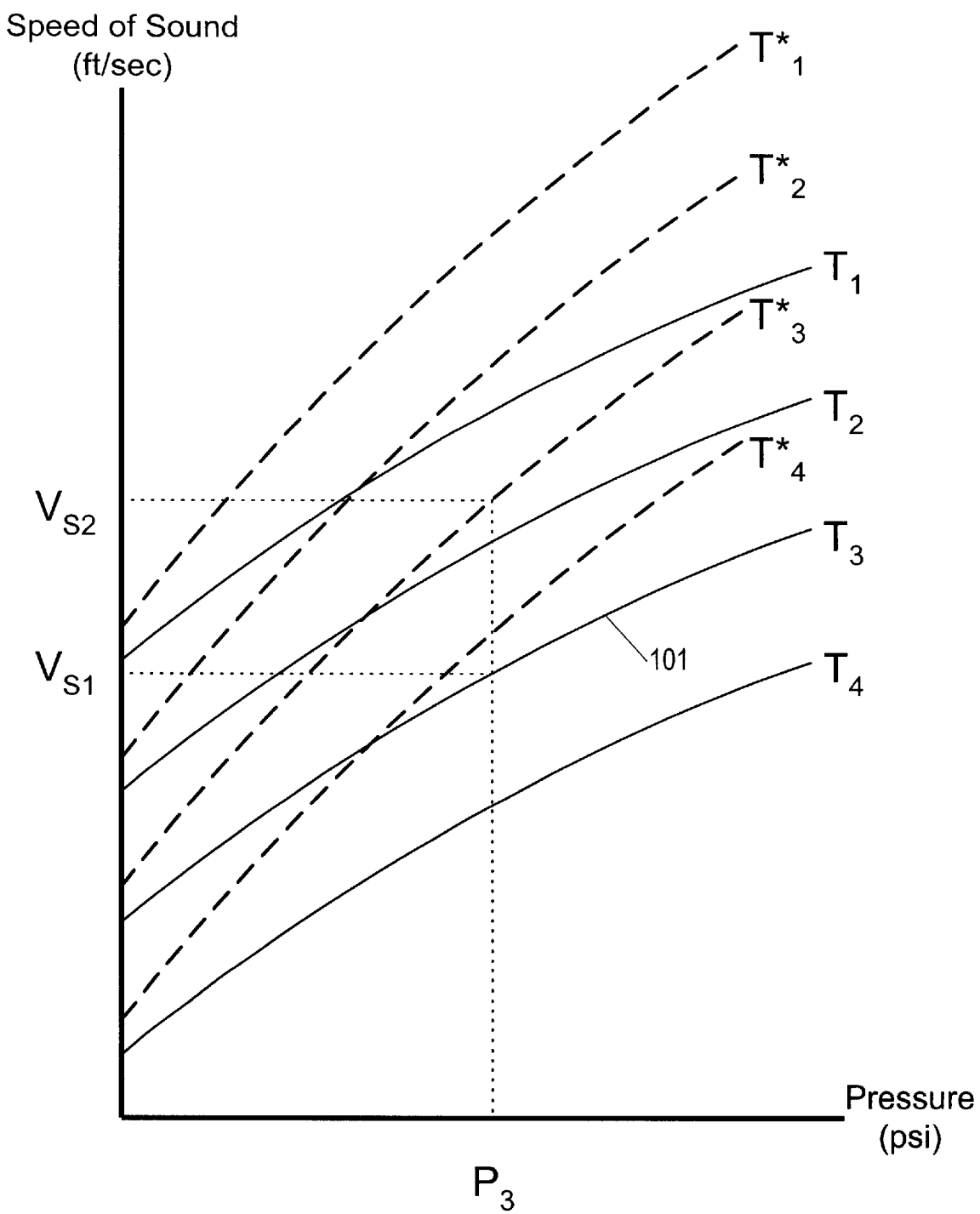
FIG. 2 is an illustration of a graph depicting, for two different fluids, the relationship between pressure, temperature and the speed of sound in each fluid.

Now referring to FIG. 2, the relationship between the speed of sound, on the one hand, and temperature and pressure, on the other hand, is shown for two different sensing materials 16a 16b. The solid curves are curves of constant temperature of one sensing material 16a, and the dashed curves are curves of constant temperature for another sensing material 16b. If the sensing material 16a is at temperature T3, and it is determined that the velocity of sound in the sensing material is $V_{S1}$, one can use the indicated relationship to infer that the pressure of the sensing material 16a is $P_3$. Of course in the problem of measuring the temperature and DC pressure of the production fluid 11, the temperature is not known. All that is known is how each mandrel 17a 17b has deformed because of the pressure and temperature of its corresponding sensing material 16a 16b, and the speed of sound in each of the fluids.

Thus, narrowband light source and signal processing module ma 30 is faced with the task of determining the DC pressure and temperature of the production fluid 11, assumed to be the same as for the sensing materials 16a 16b (because of the DC pressure and temperature coupling of the sensing materials to the production fluid provided by the membrane 15a 15b), given the speed of sound in the first fluid sensor 10a, and given the speed of sound in the second fluid sensor 10b (both speeds as determined by the narrowband light source and signal processing module 30 from the pressure wave time of flight measurement).

To perform the task, the narrowband light source and signal processing module 30 searches for one value of pressure and one value of temperature that gives both the measured speed of sound v1 (a function of pressure and temperature) in the first sensing material 16a and also the measured speed of sound v2 (a different function of pressure and temperature) in the second sensing material 16b. In other words, the two fluid sensors 10a 10b provide two pieces of information, $V_1$ and $V_2$, where:

$$V_1 = f_1(P,T), \text{ and} \quad (1)$$

$$V_2 = f_2(P,T), \quad (2)$$

where $f_1$ and $f_2$ are different functions expressing the different relationship between the speed of sound in the first sensing material 16a and in the second fluid sensor 16b. The narrowband light source and signal processing module 30 solves, by one or another usually numerical technique such as iteration, these two equations (which are usually known only numerically).

FIG. 2 shows a portion of the function $f_1$ relating pressure and temperature to the speed of sound in the first fluid sensor 10a using solid curves, each corresponding to a different temperature as indicated. (A graph of the entire function $f_1$ would be a surface in three dimensions.) FIG. 2 also shows a portion of the function $f_2$ relating the speed of sound in the second fluid sensor 10b, using dashed curves for various temperatures as indicated. In the preferred embodiment, the average slopes of tangents to the curves of the isothermal curves for the two different sensing materials are appreciably different, as in FIG. 2. For example, it is possible to use as the first sensing material 16a a first oil having a pressure to speed tangent slope that is typically 7 psi per ft/sec and having a temperature to speed tangent slope that is typically 0.2 C per ft/sec. For the second sensing material 16b, a second oil is available with tangent slopes that in each case are typically 1.5 to 2 times the values for the first oil.

It is clear from FIG. 2 that if an independent measurement of either the DC pressure of the production fluid 11 or the temperature of the production fluid is provided, then it is only necessary to use a single fluid sensor 10a or 10b. Thus, for example, if the temperature of a sensing material 16a (assumed here to be the same as the temperature of the production fluid 11) is known by some independent measurement to be $T_3$, and if the speed of sound in the sensing material 16a is measured to be $V_{S1}$, the DC pressure of the sensing material 16a can be determined immediately to be $P_3$, by using the curve 101 for speed of sound in the sensing material at the known temperature.

It should also be clear that the present invention could use a means other than windings 18a 18b 18c around a mandrel 17a 17b to sense unsteady pressure fluctuations in a sensing material 16a 16b within the mandrel and so determine the speed of the acoustic wave in the sensing material. Other means of sensing the passage of an acoustic wave in the sensing material could also be used, such as for example piezoelectric strain sensors. To provide greater reliability in a high temperature environment, the electrical signals produced by such sensors could be converted to optical signals before being communicated to a processor that might be located away from the strain sensors.

Besides other kinds of sensing means that are non-optical, it is also sometimes advantageous, according to the present invention, to wrap an optical fiber that bears a single FBG (instead of a pair of FBGs) around a mandrel 17a 17b holding a sensing material 16a 16b so that when the mandrel deforms in response to unsteady pressure fluctuations beneath the winding, the distance between each grating line (i.e. between each region of varied index of refraction) of the FBG changes and the shift in the wavelength of light reflected from the FBG is used as an indication of the passage of the acoustic wave.

Another optical alternative for a sensing means to sense the speed of an acoustic wave in a sensing material 16a in a mandrel 17a is to use not FBGs, but instead two optical fibers, with one wrapped around the mandrel and one not so wrapped, but positioned so as to be insensitive to the propagation of an acoustic wave in the sensing material. Then to sense unsteady pressure fluctuations beneath the wrapped optical fiber, light is introduced into both optical fibers and combined so as to make possible observing a variation in the interference of the light from the two optical fibers, as in a Michaelson interferometer, when the acoustic wave moves beneath the wrapped optical fiber.

Scope of the Invention

It is to be understood that the above-described arrangements are only illustrative of the application of the principles of the present invention. Numerous modifications and alternative arrangements may be devised by those skilled in the art without departing from the spirit and scope of the present invention, and the appended claims are intended to cover such modifications and arrangements.

What is claimed is:

1. A DC pressure and temperature sensor system, for sensing and measuring the DC pressure and temperature of a production fluid in tubing, comprising: a fluid sensor including a sensing material in which sound travels at a rate that depends on the DC pressure and temperature of the sensing material, the sensing material coupled to the production fluid so as to be at a DC pressure and temperature that can be correlated to the DC pressure and temperature of the production fluid, the fluid sensor responsive to the DC pressure and temperature of the production fluid via the coupling of the production fluid to the sensing material, for providing sensing signals containing information about the DC pressure and temperature of the production fluid, thereby enabling a determination of the DC pressure and temperature of the production fluid given one item of further information related to the DC pressure of the production fluid or to the temperature of the production fluid or related to the DC pressure and temperature of the production fluid in combination.

2. The DC pressure and temperature sensor system of claim 1, further comprising a sensing means including a winding of an optical fiber about a mandrel in which the sensing material is contained, the winding having a Bragg grating kept physically separated from the production fluid.

3. The DC pressure and temperature sensor system of claim 1, wherein the sensor signals are derived solely from monitoring the speed of sound in the sensing material.

4. The DC pressure and temperature sensor system of claim 1, wherein the sensing material is held in a container so as not to be able to flow out of the container, the container including a thin-walled membrane for only a relatively small portion of the entire surface of the container, the thin-walled membrane providing the coupling of the sensing material to the production fluid.

5. A DC pressure and temperature sensor system, for sensing and measuring the DC pressure and temperature of a production fluid in production tubing, comprising: a first fluid sensor and a second fluid sensor, the first fluid sensor including a first sensing material and the second fluid sensor containing a second sensing material in which sound travels at a rate that depends on the DC pressure and temperature of the second sensing material in a measurably different way than for the first sensing material, each sensing material coupled to the production fluid so as to be at a DC pressure and temperature that can be correlated to the DC pressure and temperature of the production fluid, each fluid sensor responsive to the DC pressure and temperature of the production fluid via the coupling of the production fluid to the sensing materials, for providing sensing signals containing information about the DC pressure and temperature of the production fluid.

6. The DC pressure and temperature sensor system of claim 5, wherein each fluid sensor comprises:

a) a mandrel, enclosing the respective sensing material, responsive to changes in DC and acoustical pressure and temperature of the corresponding sensing material, for providing a change in diameter corresponding to changes in DC and acoustical pressure and temperature of the corresponding sensing material;

b) an array of sensing means affixed to the mandrel, responsive to changes in the diameter of the mandrel, for providing the signals containing information about the DC pressure and temperature of the production fluid.

7. The DC pressure and temperature sensor system of claim 6, wherein at least one sensing means is a winding of an optical fiber about the mandrel, the winding having an associated Bragg grating, and is responsive to a narrowband light signal.

8. The DC pressure and temperature sensor system of claim 7, further comprising a first and second mandrel housing enclosing the first and second fluid sensor, respectively, so as to leave an air gap in which the mandrels of the first and second fluid sensor can change in diameter and to shield the first and second fluid sensors from pressure exerted by any material in the region outside the production tubing where the first and second fluid sensors are located.

9. The DC pressure and temperature sensor system of claim 7, wherein the first sensing material is a type of oil.

* * * * *

UNITED STATES PATENT AND TRADEMARK OFFICE
CERTIFICATE OF CORRECTION

PATENT NO. : 6,351,987 B1
DATED : March 5, 2002
INVENTOR(S) : Winston et al.

It is certified that error appears in the above-identified patent and that said Letters Patent is hereby corrected as shown below:

Column 3,
Line 19, please delete "it".
Line 36, please delete "lob" and substitute -- 10b -- therefor.

Column 5,
Line 22, please delete "ma".

Signed and Sealed this

Eighteenth Day of June, 2002

*Attest:*

*Attesting Officer*

JAMES E. ROGAN
*Director of the United States Patent and Trademark Office*